United States Patent [19]

Mochizuki et al.

[11] Patent Number: 5,668,402
[45] Date of Patent: Sep. 16, 1997

[54] SEMICONDUCTOR DEVICE

[75] Inventors: Kazuhiro Mochizuki, Kodaira; Shigeo Goto, Tsukuba; Chushirou Kusano, Tokorozawa; Masahiko Kawata; Hiroshi Masuda, both of Hachioji; Katsuhiko Mitani, Kodaira; Susumu Takahashi, Tokyo, all of Japan

[73] Assignee: Hitachi, Ltd., Tokyo, Japan

[21] Appl. No.: 66,635

[22] Filed: May 24, 1993

Related U.S. Application Data

[63] Continuation of Ser. No. 675,075, Mar. 25, 1991, abandoned.

Foreign Application Priority Data

Mar. 28, 1990 [JP] Japan .................. 2-076882

[51] Int. Cl.$^6$ .................. H01L 29/04
[52] U.S. Cl. .................. 257/627; 257/628
[58] Field of Search .................. 357/60, 61; 257/627, 257/628

[56] References Cited

U.S. PATENT DOCUMENTS

| | | | |
|---|---|---|---|
| 4,050,964 | 9/1977 | Rode | 257/627 |
| 4,122,407 | 10/1978 | Van Vechten | 331/94.5 H |
| 4,987,472 | 1/1991 | Endo et al. | 357/60 |

FOREIGN PATENT DOCUMENTS

| | | |
|---|---|---|
| 0 032 042 | 7/1981 | European Pat. Off. . |
| 3 728 524 A1 | 3/1988 | Germany . |
| 2 195 050 | 3/1988 | United Kingdom . |

OTHER PUBLICATIONS

Ghandi, S.K., *VLSI Fabrication Principles*, John Wiley, 1983, pp. 248–264.

Etoh et al., "Influence of Substrate Orientation on the Characteristics of $Si_{1-x}Ge_x/Si$ Strained Layers Grown by MBE", *Journal of Crystal Growth*, pp. 263–268, vol. 99, No. 1/4, Jan. 1990.

Wang et al., "Crystal orientation dependence of silicon doping in molecular beam epitaxial AlGaAs/GaAs heterostructures", *Appl. Phys. Lett.*, pp. 826–828, vol. 47 No. 8, Oct. 15, 1985.

Ilegems, "Beryllium doping and diffusion in molecular-beam epitaxy of GaAs and $Al_xGa_{1-x}As$", *Journal of Applied Physics*, pp. 1278–1287, vol. 48, No. 3, Mar. 1977.

Japanese Journal of Applied Physics, vol. 26, No. 3, Mar. 1987, pp. 439–443, An Indium–Free MBE Growth of AlGaAs/GaAs HBTs, Hiroshi Ito and Tadao Ishibashi.

1989 Electronic Materials Conference Abstracts, pp. 57–58.

*Primary Examiner*—Sara W. Crane
*Attorney, Agent, or Firm*—Kenyon & Kenyon

[57] ABSTRACT

A semiconductor device comprises a semiconductor substrate formed by a first single crystalline semiconductor material and semiconductor layers formed on the semiconductor substrate by a second single crystalline semiconductor material doped with an element which can easily surface segregate. The surface of the semiconductor substrate is formed of a crystalline plane substantially equivalent to a facet plane which is formed on the surface of the second single crystalline semiconductor material if the second single crystalline semiconductor material is epitaxially grown with being doped with the element on a (100) plane of the first single crystalline semiconductor material.

19 Claims, 3 Drawing Sheets

SEMICONDUCTOR DEVICE

This application is a continuation of application Ser. No. 07/675,075 filed on Mar. 25, 1991, now abandoned.

BACKGROUND OF THE INVENTION

The present invention relates to a semiconductor device using epitaxially grown semiconductor layers.

A semiconductor device using epitaxially grown semiconductor layers having a diamond structure or a zincblende structure has so far been produced on a (100 semiconductor) substrate, i.e., a substrate having a Miller index of 100. For example, an AlGaAs/GaAs heterojunction bipolar transistor produced on a GaAs (100) substrate is discussed in the Japanese Journal of Applied Physics 26 (1987), pp 439–443.

There has also been a case in which a semiconductor device is produced on a substrate which is misoriented by a few degrees from (100). For example, a pn-junction diode produced on a GaAs substrate which is misoriented by six degrees from (100) is reported in the 1989 Electronic Materials Conference Abstracts, pp 57–58.

SUMMARY OF THE INVENTION

The present invention provides a semiconductor device of excellent characteristics having a smooth interface of semiconductor layers with a small number of crystalline defects.

The present invention also provides a semiconductor device which has a smooth interface of semiconductor layers with a small number of crystalline defects and which can be operated at a high speed.

When a Be-doped GaAs layer was molecular beam epitaxially grown at 630 degree C. on a substrate of GaAs (100) (±0.5°) by using a prior art technique, for example, the surface of the epitaxially grown layer was atomically smooth when the carrier concentration was not higher than $3 \times 10^{19}$ cm$^{-3}$ at a room temperature. However, it was made clear that there occurs surface roughening when the film thickness exceeds 400 Å under the carrier concentration of $6 \times 10^{10}$ cm$^{-3}$ and the size of surface roughness reaches the height of 30 Å and 300 Å when the thickness of the grown layer is 400 Å and 1600 Å, respectively.

A technique for having high concentration of an impurity is essential for high performance of a semiconductor device. However, a three-dimensional growth mode which cause surface roughness may easily lead to a generation of crystalline defects such as dislocation which results in poor crystalline quality of the semiconductor layer, in contrast to a two-dimensional growth mode which ensures growth of a smooth surface layer on an atomic layer level. The above crystalline deterioration further affects the semiconductor layer which subsequently grows on a rough surface. This leads to a reduction in the carrier life time with a result of poor characteristics of the semiconductor device. The rough semiconductor layer interface invites an increase in interface roughness scattering in the semiconductor device like a two-dimensional electron (or a two-dimensional hole) gas field effect transistor in which a carrier moves in parallel with the interface, so that high frequency characteristics are also deteriorated. When the epitaxial growth temperature of the semiconductor layer is lowered by at least 200 degrees C. from the conventional level, the smoothness of the interface is improved but it is difficult to realize a high-performance semiconductor device because crystalline quality is deteriorated by low temperature growth.

Surface roughness also occurred on the epitaxially grown layer when a GaAs layer doped with tin (Sn) in high concentration, which may easily segregate like Be, was grown on GaAs (100) substrates or when a Si layer doped in high concentration with an element like boron (B) or gallium (Ga) or antimony (Sb), which may easily segregate, was grown on Si (100) substrates.

In this case, an atom which may easily segregate refers to an atom having characteristics such that, when a second semiconductor layer not including this atom is epitaxially grown on a first semiconductor layer including a plurality of this atom, the number of the atom which move toward the second semiconductor layer is larger than the quantity determined by heat diffusion.

The present invention provides a high-speed operating semiconductor device which achieves improved crystalline qualtiy, reduction in interface roughness scattering and high concentration of a dopant, by restricting surface roughening and by realizing smoothness of the semiconductor layer interface.

The present invention achieves the above characteristics by having a semiconductor device produced by growing a semiconductor layer on a semiconductor substrate having a crystalline surface equivalent to a facets surface which is generated when a semiconductor layer is grown on a substrate with (100) orientation.

The inventors of the present inventions have found, as a result of detailed observation of the above-described rough surface, that facets appeared on the surface. It is the first time that such a phenomenon has been discovered. The facets appeared along with an increase in the doping level of an element which can easily surface segregate. In this case, the facet refers to a smooth surface of an atomic level whose surface is energetically stable and has a slow growth rate.

As a result of various studies by the inventors to find a method for preventing an appearance of the above facet, it was found that an epitaxially grown layer can be produced to have no facets on a semiconductor substrate having a surface equivalent to the facet surface. The present invention is based on the above discovery, according to which the semiconductor layer and the crystalline quality of the semiconductor layer which grows on the above semiconductor layer are improved so that the characteristics of the semiconductor device can be improved.

By taking an example of the Be-doped GaAs layer, the effect of restricting an appearance of a facet will be explained with reference to FIG. 1. A semi-insulated GaAs substrate 1 was placed in a molecular beam epitaxial growth chamber, for example, to be heated to the temperature of 630 degrees C. at the As$_4$ pressure of about $1 \times 10^{-5}$ Torr and a native oxide formed on the surface was removed. An undoped GaAs layer 2 was grown to the thickness of 1600 Å at a growth rate of 1 μm/hour in order to make the surface atomically smooth. The atomical smoothness of the surface was confirmed by reflection high-energy electron-diffraction. Then, a Be-doped GaAs layer 3 (Be: $6.0 \times 10^{19}$ cm$^{-3}$) was grown to the thickness of 1600 Å and the degree of surface roughness was examined by observing the cross section of the layer by scanning and transmission electron microscopes. FIG. 1A shows a schematic diagram of the cross sectional structure of the samples. A facet 4 of {411}A appears on the surface of the Be-doped GaAs layer 3 when the GaAs (100) substrate is used for the substrate 1, as schematically shown in FIG. 1B. The GaAs (411)A surface is a surface which is misoriented by 19.5 degrees from (100) surface toward (111)A surface. Here (111)A surface means (111)Ga surface. From the fact that an appearance of a facet was not seen when the Be concentration was $3.0 \times 10^{19}$ cm$^{-3}$, it is considered that a surface roughness occurs at a concentration level when surface segregation has clearly occurred or at a higher concentration level, and the rough surface is attributable to a three dimensional growth mode where the surface-segregated Be atoms act as nucleation centers.

FIG. 1C shows degrees of surface roughness of the Be-doped GaAs layer (Be: $6.0 \times 10^{19}$ cm$^{-3}$) 3 having the film thickness of 1600 Å when the surface of the substrate 1 is misoriented from (100) toward (111)A. The surface became smoother as the substrate misorientation from (100) toward (111)A increased, and the surface roughness reached a minimum of less than 10 Å which is a measurement resolution when a (411)A substrate was used. When (411)A substrate was used, the surface smoothness was maintained even if the Be concentration was increased to $1.0 \times 1.0^{20}$ cm$^{-3}$. On the other hand, the surface roughness reached the thickness of about 15 Å and 30 Å when the (511)A substrate and (311)A substrate were used, respectively. The substrate misorientations of these substrates from (411)A is 3.7 degrees and 5.7 degrees, respectively. In the normal semiconductor device, the surface can be regarded to be practically smooth when the surface roughness is restricted to be 30 Å or below. Therefore, when the substrate misorientation from (411)A is within 6 degrees, this is practically sufficient. However, the effect of interface roughness scattering is directly reflected in the semiconductor device like a field effect transistor where a carrier moves in parallel with the semiconductor layer interface. Accordingly, it is desirable that the substrate to be used is as close to the (411)A surface as possible.

The effect of suppressing the surface roughness similar to that of the (411)A surface was obtained when GaAs (411)B substrate was used for the substrate. In this case, the GaAs (411)B substrate has a surface misoriented by 19.5 degrees from (100) toward (111)B, i.e., toward (111)As. From the above, it can be said that the substrate surface for the Be-doped GaAs is suitable to have a misorientation of ±6 degrees from the {411} surface.

A sharp profile of the impurity concentration can be obtained when a substrate having a misorientation from (100) of the present invention is used.

In order to measure B concentration-depth profile when the substrate having a misorientation from (100) is used with Be used as an impurity, the following samples were produced. Three kinds of substrates of (100), (411)A and (311)A were placed in a molecular beam epitaxial growth chamber, and an undoped GaAs layer having a thickness of 3000 Å, a Be-doped GaAs layer (Be concentration of $6 \times 10^{19}$ cm$^{-3}$) having a thickness of 1000 Å and an undoped GaAs layer having a thickness of 1000 Å were grown in this order. The Be concentration-depth profiles measured by secondary ion mass spectroscopy is shown in FIG. 6. As is clear from FIG. 6, the Be diffusion was suppressed with (411)A and (311)A orientations as compared with (100) orientation so that a sharp narrow profile is realized. Thus, it has become clear that, by using the substrates with (411)A and (311)A orientations, the effect of suppressing Be diffusion is obtained as well as the effect of restricting the appearance of facets.

The present invention can be similarly applied to group III-V compound semiconductors or their alloys doped with Be or Sn on the surface of the semiconductor substrate with {411} orientation or group IV semiconductor or their alloys doped with B, Ga or Sb on the surface of the semiconductor substrate with {311} orientation. Particularly, the smoothest surface has been realized when a semiconductor layer made of GaAs or group III-V compound semiconductor alloys including GaAs doped with Be grown on GaAs substrates.

According to the present invention, crystalline quality of a semiconductor layer is improved because roughness of the semiconductor layer interface due to the appearance of facets can be reduced, and characteristics of a semiconductor device improve because the interface roughness scattering is reduced. Further, high-speed operation of a semiconductor device can be realized because impurity concentration can be increased without sacrificing crystalline quality. Furthermore, according to the present invention, a high concentration with sharp impurity profiles can be achieved so that properties of a semiconductor device can be improved along with high-speed operation of the semiconductor device.

DETAILED DESCRIPTION

Embodiment 1

The present invention will be explained below by taking an example of an AlGaAs/GaAs hetero junction bipolar transistor with reference to FIGS. 2A to 2C.

Figure 1A:
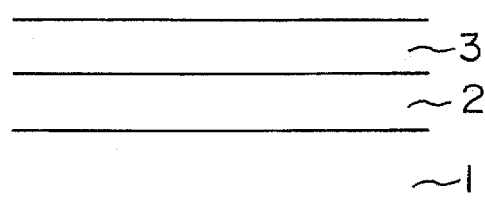
FIG. 1A is a diagram for schematically explaining the cross section structure of the samples.
Figure 1B:
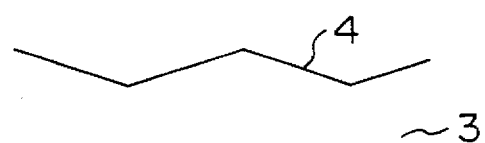
FIG. 1B is a diagram for schematically explaining the faceted surface formed on a substrate.
Figure 1C:
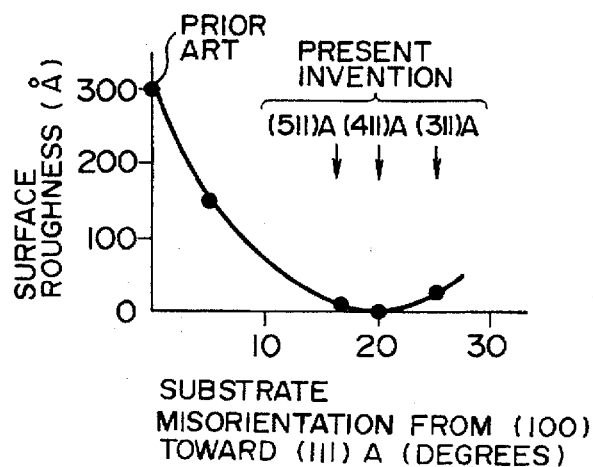
FIG. 1C is a diagram for showing the relation between the surface roughness and the substrate misorientation from (100) toward (111)A.
Figure 2A:
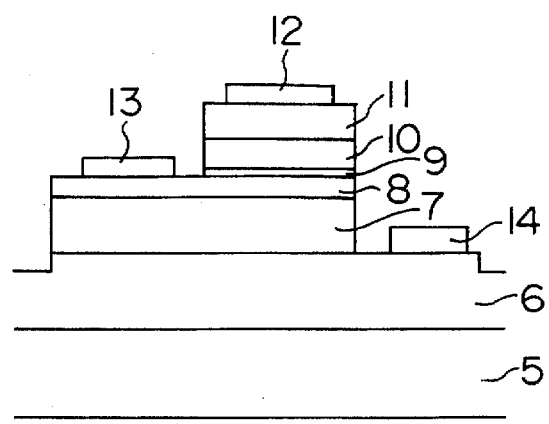
FIG. 2A is a vertical cross sectional diagram for explaining the hetero-junction bipolar transistor relating to Embodiment 1 of the present invention.

FIG. 2A is a vertical cross sectional diagram of a hetero-junction bipolar transistor produced on a substrate of GaAs (411)A. Each semiconductor layer is produced by the known molecular beam epitaxial growth method or metal organic vapor phase epitaxial growth method. The semiconductor layers are grown at 630 degrees C. at the growth rate of 1 μm/hour. The semiconductor layers are grown from the bottom in the order of a GaAs (411)A substrate 5, a high-doped n-type GaAs layer 6 (Si: $5 \times 10^{18}$ cm$^{-3}$) having a film thickness of 6000 Å, an n-type doped GaAs layer 7 (Si: $5 \times 10^{16}$ cm$^{-3}$) having a film thickness of 4000 Å, a high-doped p-type GaAs layer 8 (Be: $6 \times 10^{13}$ cm$^{-3}$) having a film thickness of 800 Å, an undoped GaAs layer 9 having a film thickness of 300 Å, an n-type doped $Al_{0.3}Ga_{0.7}As$ layer 10 (Si: $1 \times 10^{18}$ cm$^{-3}$) having a film thickness of 2000 Å and a high-doped n-type GaAs layer 11 (Si: $5 \times 10^{18}$ cm$^{-3}$) having a film thickness of 2000 Å. The surfaces of the layers 8 and 6 are exposed by photolithography and etching, and an emitter electrode 12, a base electrode 13 and a collector electrode 14 are formed, to manufacture a hetero junction bipolar transistor.

Figure 2B:
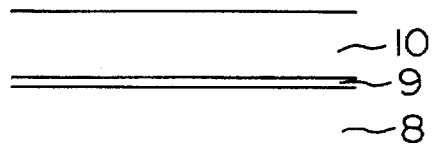
FIG. 2B is a diagram for schematically explaining the semiconductor layer interface of the transistor in FIG. 2A according to the present invention.
Figure 2C:
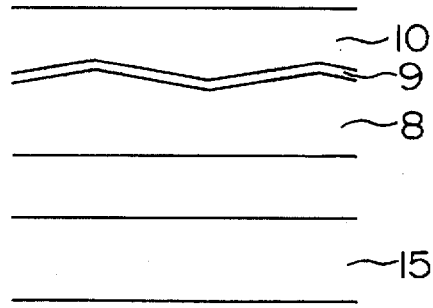
FIG. 2C is a diagram for schematically explaining the semiconductor layer interface of the transistor in FIG. 2A according to the prior art.

FIG. 2B is a schematic diagram showing an enlarged view of the portion of an interface of the layers 8, 9 and 10 in FIG. 2A. Interface roughness is not larger than 10 Å, which provides a smooth surface. On the other hand, according to the prior art technique using a GaAs (100) substrate 15, roughness occurs at the interface of the layers 8, 9 and 10, generating a roughness of about 150 Å, as schematically shown in FIG. 2C. Such roughness of the surface or interface leads to an introduction of crystalline defects such as dislocation, causing deterioration of crystalline quality. Therefore, the Be concentration can not be higher than $3 \times 10^{19}$ cm$^{-3}$. As a result, there has been a limit to reducing resistance of the base layer and accordingly a limit to the performance of the semiconductor device. According to the present embodiment, the interface is smooth and the growth is performed two dimensionally so that Be in the layer 8 can be made to have high concentration without losing crystalline quality. Since base resistance can be reduced by this arrangement, there is an effect of realizing a high-speed operating hetero junction bipolar transistor.

In the present embodiment, the film thickness of the undoped GaAs layer 9 is 300 Å which is the same as the case when the conventional (100) substrate orientation is used. However, as described in the section of operation, it is possible to restrict the diffusion of Be in the p-type GaAs layer 8 into the n-type $Al_{0.3}Ga_{0.7}As$ layer 10, so that the film thickness of the layer 9 can be reduced to be not larger than 100 Å. The smaller the film thickness of the layer 9, the less variations in the characteristics of the hetero junction bipolar transistor attributable to variations of the growth conditions. Thus, there is also an effect of improvement in the productivity.

Although GaAs is used for the layer 8 in the present embodiment, an alloy including GaAs such as AlGaAs, InGaAs or other group III-V compound semiconductor or an alloy of these may also be used for the layer 8. For the substrate, GaAs (411)B or {411} of other semiconductor may also be used.

Embodiment 2

Another embodiment of the present invention will be explained by using an AlGaAs/GaAs inversion type two dimensional hole gas field effect transistor with reference to FIGS. 3A–3C.

Figure 3A:
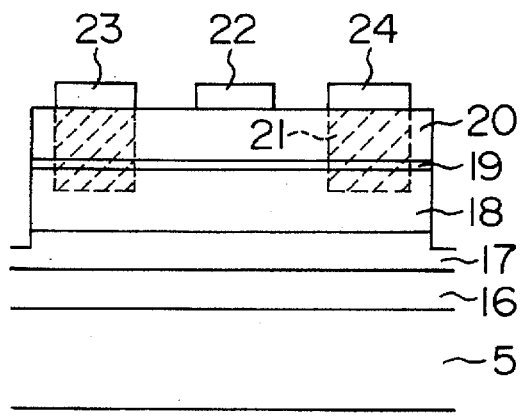
FIG. 3A is a vertical cross sectional diagram of an inversion type two-dimensional hole gas field effect transistor relating to a second embodiment of the present invention.

FIG. 3A is a vertical cross sectional diagram of an inversion type two dimensional hole gas field effect transistor produced on a substrate of GaAs (411)A. Crystals are produced by the molecular beam epitaxial growth method or metalorganic vapor phase epitaxial growth method, at the growth temperature of 630 degrees C. and growth rate 1 μm/hour. Semiconductor layers are produced from the bottom in the order of a GaAs (411)A substrate 5, an undoped GaAs layer 16 having a film thickness of 2000 Å, an undoped $Al_{0.3}Ga_{0.7}As$ layer 17 having a film thickness of 2000 Å, a high-doped p-type $Al_{0.3}Ga_{0.7}As$ layer 18 (Be: $6 \times 10^{19}$ cm$^{-3}$) having a film thickness of 3000 Å, an undoped $Al_{0.3}Ga_{0.7}As$ layer 19 having a film thickness of 300 Å and an undoped GaAs layer 20 having a film thickness of 3000 Å. A Be$^+$ ion implanting 21 is selectively carried out in the source and drain electrode formation area, and is activation-annealed at 750 degrees C. and then a device is isolated by etching. Last, a gate electrode 22, a source electrode 23 and a drain electrode 24 are formed, to produce an inversion type two dimensional hole gas field effect transistor.

Figure 3B:
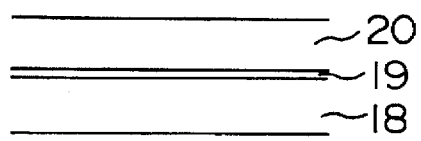
FIG. 3B is a diagram for schematically explaining the semiconductor layer interface of the transistor in FIG. 3A according to the present invention.
Figure 3C:
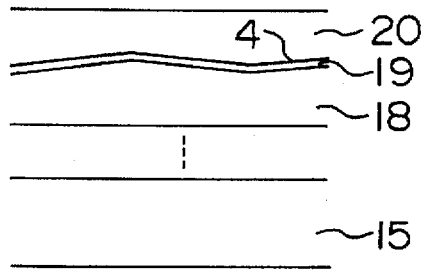
FIG. 3C is a diagram for schematically explaining the semiconductor layer interface in FIG. 3A according to the prior art.
Figure 6:
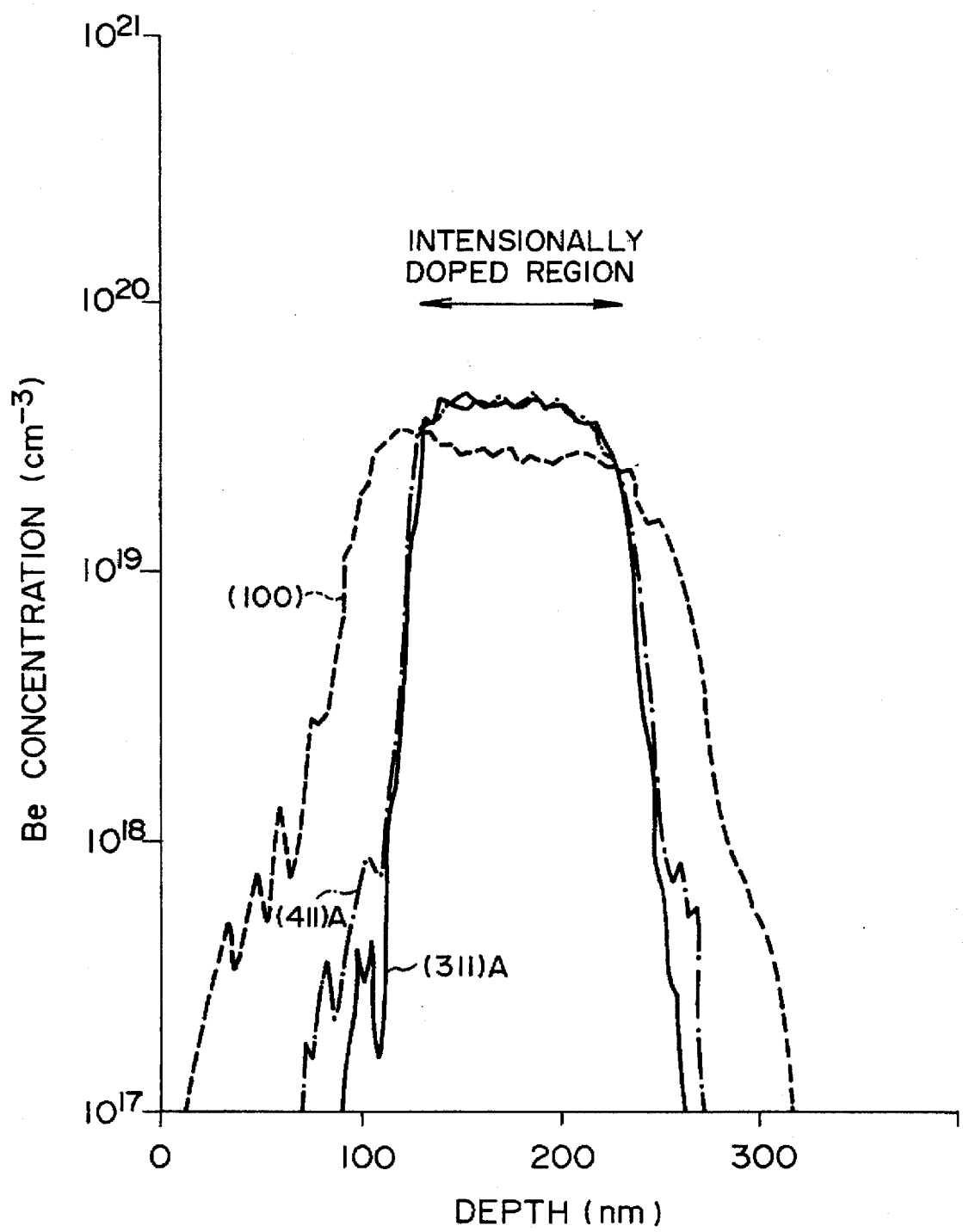
FIG. 6 is a diagram showing an impurity concentration profiles of each substrate with (100), (411)A and (311)A orientations.

FIG. 3B is a schematic diagram of an enlarged view of a portion of an interface of the layers 18, 19 and 20 in FIG. 3A. Interface roughness is not larger than 10 Å, which is regarded to be smooth. On the other hand, when the substrate 15 of GaAs (100) is used, interface roughness of the layers 18, 19 and 20 becomes about 600 Å, as schematically shown in FIG. 3C. Such interface roughness leads to an introduction of crystalline defects such as dislocation, generating a problem of deterioration in the characteristics of a semiconductor device due to deterioration of crystalline quality. Further, interface roughness invites interface roughness scattering and severely reduces mobility of the two-dimensional hole gas, resulting in extreme deterioration of the high frequency characteristics of the semiconductor device. According to the present embodiment, the interface can be made smooth so that Be in the layer 18 can have high concentration without losing crystalline quality or without increasing interface roughness scattering. By this arrangement, the sheet carrier concentration of two-dimensional hole gas can be increased and a high-speed operating inversion type two dimensional hole gas field effect transistor can be realized accordingly. Although $Al_{0.3}Ga_{0.7}As$ is used for the layer 18 in the present embodiment, the mole fraction of AlAs used here is one example and other mole fraction can also be used.

Embodiment 3

Figure 4:
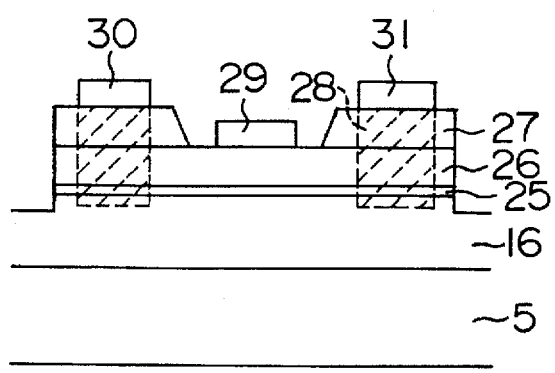
FIG. 4 is a vertical cross sectional diagram of hetero insulated gate field effect transistor with a P-type InGaAs channel relating to Embodiment 3 of the present invention.

Another embodiment of the present invention will be explained below by using a hetero insulated gate field effect transistor with p-type InGaAs channel with reference to FIG. 4.

Crystals are grown by molecular beam epitaxial growth method or metalorganic vapor phase epitaxial growth method, at the growth temperature of 480 degrees C. and with the growth rate 1 μm/hour. Semiconductor layers are grown from the bottom in the order of a GaAs (411)A substrate 5, an undoped GaAs layer 16 having a film thickness of 2000 Å, a p-type doped $In_{0.8}Ga_{0.2}As$ layer 25 (Be: $6 \times 10^{19}$ cm$^{-3}$) having a film thickness of 200 Å, an undoped $Al_{0.3}Ga_{0.7}As$ layer 26 having a film thickness of 2000 Å and a p-type doped GaAs layer (Be: $1 \times 10^{19}$ cm$^{-3}$) 27 having a film thickness of 2000 Å. The surface of the layer 26 is exposed by photolithography and by etching, and the layers 25, 26 and 27 are etched for device isolation. Be$^+$ is selectively ion implanted into the source and drain electrode formation area and activation-annealing is carried out at 750 degrees C., to form a Be$^+$ ion implanting area 28. Last, a gate electrode 29, a source electrode 30 and a drain electrode 31 are formed, to manufacture a hetero insulated gate field effect transistor.

A hereto insulated gate field effect transistor is produced by the prior art technique using a surface of GaAs (100) for the substrate. According to this method, a facet of {411}A appears on the surface 25 and the mobility of hole is lowered due to interface roughness scattering, so that high frequency characteristics of the semiconductor device are not improved. According to the present embodiment, roughness at the interface of the layers 25 and 26 becomes not higher than 10 Å, which is regarded to be smooth, so that interface roughness scattering is reduced and a semiconductor device having high performance can be realized. It is needless to mention that the mole fraction of InAs of the layer 25 is not limited to the one used above but may be flexible, and other semiconductor may also be used.

Embodiment 4

Figure 5:
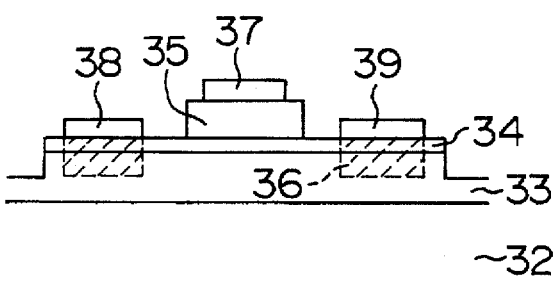
FIG. 5 is a vertical cross sectional diagram of hetero insulated gate field effect transistor with P-type Ge channel relating to Embodiment 4 of the present invention.

Another embodiment of the present invention which is applied to a hetero insulated gate field effect transistor with p-type Ge channel will be explained below with reference to FIG. 5.

Crystals are grown by molecular beam epitaxial growth method. Semiconductor layers are formed from the bottom in the order of a Si (311) substrate 32, an undoped Si layer 33 having a film thickness of 2000 Å, a Ga doped Ge layer 34 (Ga: $6 \times 10^{19}$ cm$^{-3}$) having a film thickness of 200 Å and an undoped $Al_{0.3}Ga_{0.7}As$ layer 35 having a film thickness of 2000 Å. Ga is doped in the layer 34 by the ionization doping method in order to reduce surfaced segregation. The semiconductor layers are grown at the growth rate of 1 µm/hour at the growth temperatures of 700 degrees C., 450 degrees C. and 600 degrees C. for the layer 33, the layer 34 and the layer 35 respectively. The surface of the layer 34 is exposed and devices are isolated by photolithography and by etching, and Ga$^+$ is selectively ion implanted into the source and drain formation area, with activation-annealing carried out at 750 degrees C., to form a Ga ion implanting area 36. Last, a gate electrode 37, a source electrode 38 and a drain electrode 39 are formed, to manufacture a hetero insulated gate field effect transistor.

According to the present embodiment, roughness at the interface of the layers 34 and 35 is not larger than 10 Å and interface roughness scattering is restricted, so that a high-speed operation semiconductor device can be realized. Although a p-type layer is used for the layer 34 in the present embodiment, a high performance hetero insulated gate field effect transistor with n-type Ge channel can be realized when ionization doping of Sb is used. The layer 34 is not limited to Ge, but a layer consisting of $Si_{1-x}Ge_x$ (0.9<x<1) may also be used.

In the above embodiments, 2, 3 and 4, description has been made about an application to the p-type channel FET (field effect transistor) as an example. However, the present invention can be equally applied to the n-type channel FET as well.

We claim:

1. A semiconductor device, comprising:

a semiconductor substrate of a first single crystalline semiconductor material; and a first semiconductor layer of a second single crystalline semiconductor material doped with at least one element, said first semiconductor layer being formed on or above a surface of said semiconductor substrate;

wherein the surface of said semiconductor substrate is formed of a crystalline plane having a Miller index substantially equivalent to a Miller index of a facet plane formed on a surface of a semiconductor layer of said second single crystalline semiconductor material which is epitaxially grown on a {100} plane of said first single crystalline semiconductor material, and which is doped with said at least one element, and in which said at least one element is segregated by surface segregation phenomenon on the surface of said semiconductor layer which is epitaxially grown on the {100} plane.

2. A semiconductor device according to claim 1, wherein an activated concentration of said easily surface segregatable elements exceed $3 \times 10^{19}$ cm$^{-3}$ at a room temperature.

3. A semiconductor device according to claim 1, wherein a film thickness of one of said semiconductor layers is 40 nm or above.

4. A semiconductor device according to claim 1, wherein said second single crystalline semiconductor material forming said semiconductor layers is either a group III-V compound semiconductor or an alloy of group III-V compound semiconductors, said semiconductor substrate has a diamond structure or a zincblende structure, and said semiconductor substrate surface's substrate orientation is {411} ±six degrees.

5. A semiconductor device according to claim 4, wherein said semiconductor substrate comprises GaAs and said group III-V semiconductor comprises GaAs or an alloy including GaAs.

6. A semiconductor device according to claim 4, wherein said element which can easily surface segregate is Be.

7. A semiconductor device according to claim 1, wherein said second single crystalline semiconductor material forming said semiconductor layers is a group IV semiconductor or an alloy of group IV semiconductors, said semiconductor substrate has either a diamond structure or a zincblende structure, and substrate orientation of said semiconductor substrate is within {311} ±six degrees.

8. A semiconductor device according to claim 7, wherein said group IV semiconductor or said alloy of group IV semiconductors comprises $Si_{1-x}Ge_x$ (0.9<x≤1) and said semiconductor substrate comprises Si.

9. A semiconductor device according to claim 7, wherein said element which can easily surface segregate is B, Ga or Sb.

10. A semiconductor device, comprising:

a semiconductor substrate having a substrate surface orientation of {411} ±six degrees;

a first single crystalline semiconductor layer having a first conductor type formed on said semiconductor substrate;

a second single crystalline semiconductor layer formed on said first single crystalline semiconductor layer, and including an element which can easily surface segregate as a doping impurity, having concentration exceeding $3 \times 10^{19}$ cm$^{-3}$ at room temperature for said surface segregatable element that has been activated, and having a second conductor type different from a first conductor type; and a third single crystalline semiconductor layer having a first conductor type and being formed on said second single crystalline semiconductor layer.

11. A semiconductor device, comprising:

a semiconductor substrate having a substrate surface orientation of {411} ±six degrees;

a first single crystalline semiconductor layer of a substantially undoped type formed on said semiconductor substrate;

a second single crystalline semiconductor layer formed on said first single crystalline semiconductor layer, and including an element which can easily surface segregate as a doping impurity, having concentration exceeding $3\times10^{19}$ cm$^{-3}$ at room temperature for said surface segregatable element that has been activated, and having a first conductor type;

a third single crystalline semiconductor layer of a substantially undoped type, formed on said second single crystalline semiconductor layer having said first conductor type; and a fourth single crystalline semiconductor layer of a substantially undoped type, formed on said third single crystalline semiconductor layer, and having a hetero junction formed with said third single crystalline semiconductor layer.

12. A semiconductor device according to claim 1 wherein a film thickness of each of said semiconductor layers is 40 mm or above.

13. A semiconductor device, comprising:

a semiconductor substrate having a substrate surface orientation of {311} ±six degrees;

a first single crystalline semiconductor layer having a first conductor type formed on said semiconductor substrate;

a second single crystalline semiconductor layer formed on said first single crystalline semiconductor layer, and including an elements which can easily surface segregate as a doping impurity, having concentration exceeding $3\times10^{19}$ cm$^{-3}$ at room temperature for said surface segregatable element that has been activated, and having a second conductor type different from a first conductor type; and a third single crystalline semiconductor layer having a first conductor type and being formed on said second single crystalline semiconductor layer.

14. A semiconductor device, comprising:

a semiconductor substrate having a substrate surface orientation of {311} ±six degrees;

a first single crystalline semiconductor layer of a substantially undoped type formed on said semiconductor substrate;

a second single crystalline semiconductor layer formed on said first single crystalline semiconductor layer, and including an element which can easily surface segregate as a doping impurity, having concentration exceeding $3\times10^{19}$ cm$^{-3}$ at room temperature for said surface segregatable element that has been activated, and having a first conductor type;

a third single crystalline semiconductor layer of a substantially undoped type, formed on said second single crystalline semiconductor layer having said first conductor type; and a fourth single crystalline semiconductor layer of a substantially undoped type, formed on said third single crystalline semiconductor layer, and having a hetero junction formed with said third single crystalline semiconductor layer.

15. A semiconductor device according to claim 10 wherein the semiconductor device is a hetero junction bipolar transistor.

16. A semiconductor device according to claim 13 wherein the semiconductor device is a hetero junction bipolar transistor.

17. In a field-effect transistor, a structure comprising:

a semiconductor substrate having a substrate surface orientation of {411} ±six degrees;

a first single crystalline semiconductor layer of a substantially undoped type formed on said semiconductor substrate;

a second single crystalline semiconductor layer formed on said first single crystalline semiconductor layer, and including an element which can easily surface segregate as a doping impurity, having concentration exceeding $3\times10^{19}$ cm$^{-3}$ at room temperature for said surface segregatable element that has been activated, and having a first conductor type;

a third single crystalline semiconductor layer of a substantially undoped type, formed on said second single crystalline semiconductor layer having said first conductor type; and a fourth single crystalline semiconductor layer of a substantially undoped type, formed on said third single crystalline semiconductor layer, and having a hetero junction formed with said third single crystalline semiconductor layer.

18. In a field-effect transistor, a structure comprising:

a semiconductor substrate having a substrate surface orientation of {311} ±six degrees;

a first single crystalline semiconductor layer of a substantially undoped type formed on said semiconductor substrate;

a second single crystalline semiconductor layer formed on said first single crystalline semiconductor layer, and including an element which can easily surface segregate as a doping impurity, having concentration exceeding $3\times10^{19}$ cm$^{-3}$ at room temperature for said surface segregatable element that has been activated, and having a first conductor type;

a third single crystalline semiconductor layer of a substantially undoped type, formed on said second single crystalline semiconductor layer having said first conductor type; and a fourth single crystalline semiconductor layer of a substantially undoped type, formed on said third single crystalline semiconductor layer, and having a hetero junction formed with said third single crystalline semiconductor layer.

19. A semiconductor device comprising:

a) a semiconductor substrate, said semiconductor substrate
  i) being formed of a first single crystalline semiconductor material, and
  ii) having a surface formed of a crystalline plane having a Miller index {XYZ}; and b) a first semiconductor layer, said first semiconductor layer
  i) being formed of a second single crystalline semiconductor material,
  ii) being doped with at least one element, and
  iii) being formed on or above a surface of said semiconductor substrate;

wherein said Miller index {XYZ} is substantially equivalent to a Miller index of a facet plane formed on a surface of a semiconductor layer, said semiconductor layer
  i) being formed of said second single crystalline material,
  ii) being doped with said at least one element, and
  iii) being epitaxially grown on a {100} plane of a substrate of said first single crystalline semiconductor material, and wherein said at least one element is easily surface segregated.

* * * * *

UNITED STATES PATENT AND TRADEMARK OFFICE
CERTIFICATE OF CORRECTION

PATENT NO. : 5,668,402

DATED : 16 September 1997

INVENTOR(S) : Kazuhiro MUCHIZUKI et al.

It is certified that error appears in the above-identified patent and that said Letters Patent is hereby corrected as shown below:

| Column | Line | |
|---|---|---|
| 2 | 10 | Change "toward" to --in--. |
| 2 | 28 | After "on the surface" insert --having a convex section-- |
| 9 | 24 | Change "elements" to --element--. |

Signed and Sealed this

Fourteenth Day of April, 1998

Attest:

BRUCE LEHMAN

Attesting Officer                Commissioner of Patents and Trademarks